United States Patent [19]

De Vincentiis

[11] 4,328,242
[45] May 4, 1982

[54] α-(3,4,5-TRIMETHOXYHENZOYL)THIO-PROPIONYL-GLYCINE

[75] Inventor: Leonardo De Vincentiis, Rome, Italy

[73] Assignee: Ausoria Farmaceutici S.r.l., Pomezia, Italy

[21] Appl. No.: 222,748

[22] Filed: Jan. 5, 1981

[30] Foreign Application Priority Data

Nov. 11, 1980 [IT] Italy ............................... 25883 A/80

[51] Int. Cl.³ ................. A61K 31/265; C07C 153/023
[52] U.S. Cl. .................................. 424/301; 260/455 R
[58] Field of Search ....................... 260/455 R; 424/301

[56] References Cited

U.S. PATENT DOCUMENTS 3,178,466  4/1965  McDowell et al. ............ 260/455 R

OTHER PUBLICATIONS

Reid, Organic Chemistry of Bivalent Sulfur, vol. 4, Chem. Publishing Co., Inc., New York, 1962, p. 27.

Primary Examiner—Alan L. Rotman
Assistant Examiner—Robert C. Whittenbaugh
Attorney, Agent, or Firm—Bucknam and Archer

[57] ABSTRACT

A novel compound α-(3,4,5-Trimethoxybenzoyl)propionylglycine is described. The substance is more stable than 2-mercaptopropionylglycine and is useful for the therapy of subacute and chronic pathological conditions of the bronchi, acute and chronic conditions of the liver, and for the treatment of aftermaths of intoxication.

4 Claims, No Drawings

α-(3,4,5-TRIMETHOXYBENZOYL)THIOPROPIONYL-GLYCINE

This invention relates to novel pharmaceutical compositions and more specifically, the present invention relates to a new compound:

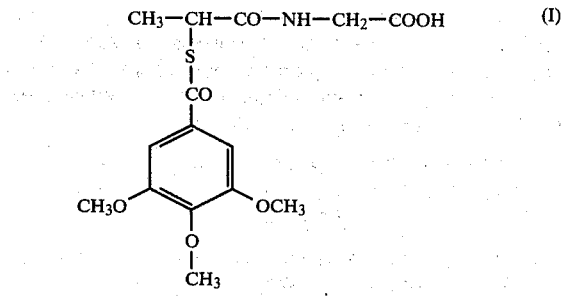

The present invention also relates to the process for the preparation of the compound of formula I. The present invention also relates to pharmaceutical compositions which contain as the active constituent the compound of formula I suitable for the treatment of acute and chronic bronchitis conditions, pathological conditions of the liver and for the treatment of conditions resulting from intoxication.

It is known that 2-mercaptopropionylglycine of formula II:

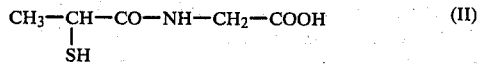

exhibits significant pharmacological activity which makes the substance suitable to protect the liver, for the treatment of acute and chronic pathological conditions of the liver and for the treatment of conditions caused by intoxication. It is also known, however, that 2-mercaptopropionylglycine exhibits low stability both in the solid state as a dry powder as well as in solution, not only when the substance is stored in normal conditions and particularly unfavorable at high temperature, high humidity, exposure to light, but also under normal conditions even at low relative humidity and at room temperature.

This low stability of the substance which manifests itself even after a relatively short period of storage, obviously causes a number of drawbacks, the worst of which undoubtedly resides in the change in the organoleptic properties with the development of odor and taste which are very unpleasant. This change causes negative psychological effects in the patients and also affects the therapeutic properties of the formulation.

It has now been found that α-(3,4,5-trimethoxybenzoyl)thiopropionylglycine of formula I as shown hereinabove, in addition to exhibiting stability which is substantially higher than the stability of compound II, and in addition to exhibiting very good pharmacological properties, which make the substance very suitable for the treatment of acute and chronic pathological conditions of the liver and suitable in the treatment of conditions resulting from intoxication, also exhibits an activity in the protection of subacute and chronic bronchitis which is substantially superior to the activity of α-mercaptopropionylglycine.

In addition to the foregoing, it has been found in the course of the experimental work that the compound of formula I exhibits optimum clinical tolerance with respect to gastric reactions, a tolerance which is the result of the stability of the product and, therefore, the lack of unpleasant odor and taste.

The process of preparation according to the present invention consists of reacting 3,4,5-trimethoxybenzoyl-chloride with 2-mercaptopropionylglycine in an aqueous medium and in the presence of a base, for instance, a carbonate or bicarbonate of an alkali metal and particularly suitable of sodium or potassium.

The following example is given by way of illustration of the invention.

EXAMPLE 3,4,5,-trimethoxybenzoyl-chloride in the amount of 21.8 grams is added under stirring to a solution containing 18 grams of 2-mercaptopropionylglycine and 40 grams of $K_2CO_3$ in 100 cc of water. Stirring is continued until the chloride has completely reacted. The mixture is then brought to a pH of about 3 with 10% $H_2SO_4$. The precipitate is filtered off, washed with water and allowed to crystallize from ethanol.

Melting Point: 175°–177° C.

The structure of the compound is confirmed by analytical and spectroscopic analysis, specifically IR and NMR spectra. The compound is in the form of a white micro-cyrstalline powder, odorless and almost tasteless. It is soluble in a saturated solution of sodium bicarbonate and in other basic solutions. The substance is insoluble in water, soluble in warm ethanol.

The pharmaco-toxicological properties of the compound of formula I are manifest from the experimental results reported hereinbelow. For the sake of brevity, the compound of formula I is designated by the symbol TBPG.

ACUTE TOXICITY

The acute toxicity has been studied with Swiss albino rats and Wistar albino rats and in both instances, animals of both sexes have been used. The product is administered orally and endoperitoneally and the period of observation is ten days after the initial treatment. The values of $DL_{50}$ by the statistical method with confidential limits up to 95% are calculated by means of the method of probits reported in Table I. Probits is a statistical unit of probable deviation used in biological assays; equal to the normal equivalent deviate increased by 5, used to make all normal equivalent deviation values positive.

TABLE I

| | Acute Toxicity in Mice and Rats | | | | | |
|---|---|---|---|---|---|---|
| Species | Administration Route | No. of Animals Tested | Dose mg/kg | No. of Animals Dead | % Death | $DL_{50}$ mg/kg (Confidential Limits) |
| Mice | Orally | 20 | 3000 | 1 | 5 | 4863 |
| | | 20 | 4000 | 6 | 30 | |
| | | 20 | 5000 | 10 | 50 | (4539–5254) |
| | | 20 | 6000 | 15 | 75 | |
| | | 20 | 7000 | 18 | 90 | |
| Mice | i.p. | 20 | 1500 | 0 | 0 | 2534 |
| | | 20 | 2000 | 8 | 40 | |
| | | 20 | 2500 | 10 | 50 | (2192–2963) |
| | | 20 | 3000 | 13 | 65 | |
| | | 20 | 3500 | 18 | 90 | |
| Rats | Orally | 20 | 3000 | 1 | 5 | 5231 |
| | | 20 | 4000 | 6 | 30 | |
| | | 20 | 5000 | 9 | 45 | (4879–5873) |

TABLE I-continued

| Species | Administration Route | No. of Animals Tested | Dose mg/kg | No. of Animals Dead | % Death | DL$_{50}$ mg/kg (Confidential Limits) |
|---|---|---|---|---|---|---|
|  |  | 20 | 6000 | 12 | 60 |  |
|  |  | 20 | 7000 | 17 | 85 |  |
| Rats | i.p. | 20 | 1500 | 0 | 0 | 2666 |
|  |  | 20 | 2000 | 6 | 30 |  |
|  |  | 20 | 2500 | 9 | 45 | (2483–2887) |
|  |  | 20 | 3000 | 14 | 70 |  |
|  |  | 20 | 3500 | 17 | 85 |  |

SUBCHRONIC TOXICITY

Treatment by the rectal route of rabbits for a period of eight consecutive weeks with TBPG (two suppositories per day, per animal equal to 400 mg/kg), has not caused any irregularities in the behavior and in the body growth of the animals. Also, the hematochemical data and data of hepatic and renal functions, as well as studies of autopsies and macro/microscopic controls of the main organs have not shown any variations from the normal.

CHRONIC TOXICITY

The chronic toxicity of TBPG has been investigated in rats and dogs treated for a period of 24 weeks with 125 mg/kg and 250 mg/kg by the oral route and 200 mg/kg by inhalation.

The treatment has resulted to be totally innocuous because no symptoms or changes in behavior have been observed and there has been no deaths. Also, other parameters which have been considered such as body growth, hematological examination. and hematochemical examination, tests of hepatic and renal functions, as well as macro and microscopic examination of the main organs have not shown any alteration worthwhile mentioning with respect to the normal behavior.

TOXICITY IN THE FETUS

Toxicity in the fetus of TBPG has been studied in albino Sprague-Dawley rats and in New Zealand rabbits. In the case of rats both male and female, the treatment has been initiated four weeks prior to coupling and then has been continued only in the females during the twenty days of gestation.

In the case of female rabbits, the treatment has been carried out during the twenty eight days of gestation. The daily administration of TBPG through the oral route and the subcutaneous route in the dosage of 250 and 500 mg/kg has not induced any deformation in the fetus and has not affected the number and the weight of the living offspring.

PHARMACODYNAMICS

The substance TBPG up to a dose of 50 mg/kg intravenously has exhibited very high tolerance in anaesthesized cats. In fact, the substance causes only a low and temporary reduction in the arterial pressure without any effect on the cardiac frequency on the respiratory dynamics and on the electrocardiogram.

PHARMACOLOGICAL ACTIVITY

Protective Activity in Subacute Bronchitis Induced by Inhalation of Citric Acid in Guinea Pigs The substance TBPG administered by the oral route, rectal route, or by inhalation in dosages of 50 and 200 mg/kg respectively for a period of two weeks has exhibited an effective protective action in proportion to the dose in the treatment of the bronchial conditions induced experimentally in guinea pigs by inhalation of a 7.5% solution of citric acid. This protective action has been confirmed both by a macro and micro examination carried out in the lungs and by the mortality index which is substantially reduced by treatment with TBPG. The effectiveness of the substance being examined has resulted essentially overlapping with the efficacy of α-mercaptopropionylglycine which has been used for comparison and which has been administered by the oral route in equimolar doses.

PROTECTIVE ACTION ON CHRONIC BRONCHITIS INDUCED BY INHALATION OF SO$_2$ RATS

Bronchopulmonary lesions were induced in the animals by aerosolization of SO$_2$. The animals were then treated for two weeks with TBPG in the dosage of 100 and 400 mg/kg by the oral route, rectal route and by inhalation. Also, in this case, as it has been noted in the previous experiment, TBPG has exerted a significant action in the protection of the bronchi and lungs, both in regard to the bronchopulmonary lesions, as well as in the mortality of the animals. Analogous results have been obtained with equimolar dosages of α-mercaptopropionylglycine.

SECRETORY ACTIVITY IN RABBITS

This activity has been determined using the method described by E. M. Boyd and C. F. Boyd, modified by P. C. Braga, et al described in Bronchial Hypersecretion, 1973. This activity has been determined every hour for a period of four hours by measuring the amount of bronchial secretion derived from the laryngo-tracheal organs and from the tracheo-bronchial organs of rabbits. The substance TBPG administered by the oral route, rectal or by inhalation in the dosage of 50 and 200 mg/kg has exhibited the ability to increase in a significant manner and proportionally to the dosage, the laryngo-bronchial secretion in rabbits. The activity of the substance has resulted equal to the activity of α-mercaptopropionylglycine in the value of the laryngo-tracheal secretion (P 0.05 with respect to the control animals). Very significantly though, more substantial activity with respect to the tracheo-bronchial secretion has been noted, (in the case of TBPG, Pα 0.05 with respect to the control animals); α-mercaptopropionylglycine = n.s.

BRONCHOSECRETOLITHIC ACTIVITY IN RATS

The secretolithic activity of TBPG has been determined in comparison to α-mercaptopropionylglycine by administering 300 mg/kg of the substance intraperitonally and comparing with 135 mg/kg of 60-mercaptopropionylglycine administered also intraperitoneally. The doses are equimolar. The method is based on the use of sodium fluorescine described by H. M. Mawatari (Experimental Studies on the Expectorant Action of Several Drugs, Kogoshima Daigakeu Igakeu Zasshi 27, 561, 1976).

On the basis of the results obtained, it is possible to conclude that the bronchosecretolithic activity of TBPG is much higher than that of α-merceptopropionylglycine, that is 34.4% while in the case of the animals treated with the control substance, the result is only 15.2%.

ANTIBRONCHOSPASTIC ACTIVITY IN GUINEA PIGS

This test has been carried out as follows:

Histamine administered in the form of an aerosol has caused in guinea pigs symptoms of broncho-spasm accompanied by convulsions, irreversible collapse and death. TBPG administered by the oral route, the rectal route or by inhalation in the dose of 200 and 400 mg/kg has increased very substantially the period of time between the administration of the aerosol and the appearance of the bronchospastic symptoms with an efficacy comparable equimolar doses of α-mercaptopropionylglycine.

PROTECTIVE ACTIVITY OF THE LIVER IN THE INTOXICATION CAUSED BY CCl₄

The animals, that is rats, were intoxicated with $CCl_4$ for a period of seven days. They were treated during the same days and for a subsequent period of seven days with TBPG in the dose of 200 and 400 mg/kg orally and with 60-mercaptopropionylglycine in the dose of 90 and 180 mg/kg orally. On the fifteenth day, the rats have been treated with BSF in the amount of 10 mg/kg intravenously.

The determination of the hematic concentrations of BSF has permitted to show that the administration of TBPG favors the elimination of BSF in a statistically significant manner in rats intoxicated with $CCl_4$. This action results proportionate to the dosage and is comparable to the action exerted by equimolar doses of α-mercaptopropionylglycine.

REGENERATIVE ACTION IN PARTIAL HEPATECTOMY

TBPG administered by the oral route in the dose of 200 and 400 mg/kg of a period of six days in rats previously subjected to partial hepatectomy with excision of 70% of the entire organ, has exhibited the ability of favoring the regeneration of the hepatic tissue in statistically significant manner comparable to the activity exerted by equimolar doses of α-mercaptopropionylglycine.

ACTION ON THE PERIOD OF SLEEP INDUCED BY BARBITURATES

The activity of TBPG administered for two days in the dose of 200 and 400 mg/kg orally, has been determined on the basis of the reduction of the period of sleep induced by Nembutal on rats intoxicated with $CCl_4$.

The activity of TBPG which manifests itself to be very substantial and with a clear correlation between dosage and effect, results essentially comparable to the activity exerted by equimolar doses of α-mercaptopropionylglycine.

ACTION ON THE GLUTATHIONE PEROXIDASE (GSHP)

The experiment has been carried out for the purpose of determining the inhibitory activity if any of TBPG with respect to GSHP, an enzyme well known connected with phlogistic processes.

The results have been obtained using the system glutathione/NADPH/GSH-reductase/cumene hydroperoxide and have shown that TBPG is capable of exerting an inhibitory activity on GSHP with an apparent Ki $5.4.10^{-3}$ molar.

BIOCHEMICAL STUDIES ON METABOLISM

After administration through the oral route in rats of equimolar doses of TBPG and α-mercaptopropionylglycine, the distribution in the organs results to be sufficiently homogenous with the exception for both substances of having high concentrations in the kidney.

However, in the case of TBPG, there is noted, a substantially higher content in the lungs, a fact which is statistically significant with respect to α-mercaptopropionylglycine. This fact appears to be attributable to a significant pulmonary tropism exhibited by TBPG.

In addition to the pharmacological advantages mentioned hereinabove, the compound according to the invention exhibits organoleptic properties substantially superior to α-mercaptopropionylglycine, which properties are due to the superior stability of the substances as it will be demonstrated by the experiments reported hereinbelow.

PROPERTIES AND LIMITATIONS OF STABILITY OF TBPG IN COMPARISON WITH α-MERCAPTOPROPIONYLGLYCINE (MPG) AND DEGRADATION PRODUCTS, IF ANY

Stability at Room Temperature

Five different samples of TBPG and α-mercaptopropionyl glycine have been preserved at room temperature in closed containers for a period of 36 months. At the end of the storage period, the following properties have been determined:

Taste
Odor
Chromatography
Infrared Spectrum

The results which have been obtained have shown that while the two substances do not exhibit any change from a physical-chemical point of view, the organoleptic properties of α-mercaptopropionylglycine undergo substantial change.

ISOTHERMIC STABILITY ACCORDING TO THE METHOD OF GARRET

The tests of accelerated stability have been carried out with the substance in powder form, that is in glass vials, hermetically closed with a plastic screw cap and also with the substance dissolved in water, that is 500 mg in 10 cc in a transparent glass container of 20 cc capacity closed with a plastic screw cap.

The production of impurities, if any, due to degradation of the substance, has been determined by means of TLC. The conditions being used, the period of time and the results obtained are reported in Table 2. The chromatographic impurities exhibited by the sample of TBPG results would be due to α-mercaptopropionylglycine which is formed by hydrolysis of TBPG.

STABILITY TO LIGHT

The substance TBPG in a powder form, exposed to the light of a 60 watt lamp for a period of three months undergoes no change while MPG exhibits a strong yellow color, due to degradation accompanied by an unpleasant odor and taste.

TABLE 2

Results of Tests of Accelerated Stability

| Temperature | Time in Hours | Chromatographic Impurities | | | |
|---|---|---|---|---|---|
| | | Powder | | Solution | |
| | | TBPG | MPG | TBPG | MPG |
| 60° | 0 | — | — | Absent | Absent |
| | 320 | Absent | Traces | " | 0.5% |
| | 640 | " | " | 0.5% | 0.6% |
| | 960 | " | 1% | 0.7% | 1% |
| | 1280 | " | 1% | 1.2% | 1.5% |
| | 1600 | " | 2% | 1.3% | 2.5% |
| 70° | 120 | Absent | Traces | — | — |
| | 180 | — | — | Absent | 1% |
| | 240 | Absent | 1% | 1.1% | 2% |
| | 480 | " | 2% | 1.2% | 2.5% |
| 80° | 45 | Absent | 1% | Absent | 1% |
| | 90 | " | 1% | 1.2% | 2.5% |
| | 120 | — | — | 1.3% | 1.5% |
| | 180 | Absent | 2% | — | — |

STABILITY TO MOISTURE

Samples of TBPG and MPG have been maintained in open vials at room temperature under conditions of 90% relative humidity and at 50° C. always with 90% relative humidity. After a month of exposure, the following observations have been made.

TBPG-t.a.=no decomposition

50° C.=slight yellow color, but no degradation products

MPG-t.a.=significant change of organoleptic properties

50° C.=marked change in color, odor and taste accompanied by degradation products

STABILITY IN SOLUTION

Acidic medium: both compounds placed in an acidic solution, 10% 0.1 normal HCl at 60° C. for five days do not undergo degradation Alkaline medium: both substances placed in an alkaline solution of 10% 0.1 normal NaOH at 60° C. for five days undergo degradation Oxidizing medium: both substances maintained in the presence of 3% hydrogen peroxide for a period of two months undergo substantial decomposition, but the change is greater for MPG.

REDUCING MEDIUM

In the presence of $SO_2$—solutions containing 25 mg/ml of TBPG and MPG respectively in the presence of sodium bisulfite calculated as $SO_2$ are warmed and refluxed for a period of three hours. TBPG undergoes no physico-chemical change or organoleptic change. MPG, on the other hand, undergoes substantial physico-chemical and organoleptic change.

CONCLUSIONS

On the basis of the tests, the conclusion is reached that the substance TBPG is substantially more stable than α-mercaptopropionylglycine both in the dry state, as well as in a moist atmosphere under different conditions of storage.

α-mercaptopropionylglycine undergoes significant changes from the organoleptic point of view, a fact which is not observed in the case of TBPG. Also from the physico-chemical point of view, TBPG is more stable than α-mercaptopropionylglycine.

The substance according to the present invention may be administered through the oral or parenteral route in various pharmaceutical formulations, for instance:

Capsules, Tablets or Compresses containing 500 mg of the active substance

Phthials to be used peritoneally and in the aerosol form containing 250-500-1000 mg Syrups of 2%-3%-4% concentration Suppositories for Adults containing 400 mg of the active substance Suppositories for Children containing 200 mg of the active substance Suppositories for Breast-Feeding Mothers containing 100 mg Envelopes with the substance in granular form of 4% concentration Conventional carriers and excipients are incorporated in the compositions.

What is claimed is:

1. α-(3,4,5-Trimethoxybenzoyl)thiopropionylglycine of formula (I)

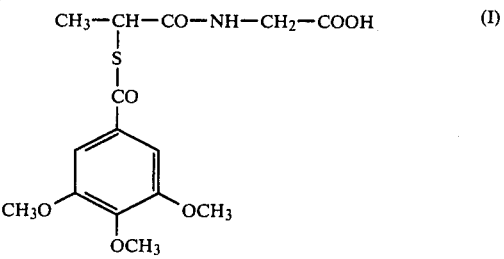

2. A pharmaceutical composition for the therapy of subacute and chronic bronchitis, bronchopulmonary lesions, bronchospastic conditions, hepatic insufficiency, intoxication of the liver in unit dosage form to be administered orally or parenterally, which comprises an effective amount of α-(3,4,5-trimethoxybenzoyl)thiopropionylglycine and at least one pharmaceutically compatible carrier or excipient.

3. The method of treatment of subacute and chronic bronchitis, bronchopulmonary lesions, or bronchospastic conditions, which consists of administering to a living subject affected by one of said conditions, an effective amount of α-(3,4,5-trimethoxybenzoyl)thiopropionylglycine of formula I.

4. The method of treatment of subacute and chronic hepatic insufficiency and intoxication of the liver, which consists of administering to a living subject affected by one of said conditions, an effective amount of α-(3,4,5-trimethyoxybenzoyl)thiopropionylglycine of formula I of claim 1.

* * * * *